(12) United States Patent
Edlund et al.

(10) Patent No.: US 8,467,873 B2
(45) Date of Patent: Jun. 18, 2013

(54) SYNCHRONIZATION METHODS AND DEVICES IN TELEMETRY SYSTEM

(75) Inventors: Pär Edlund, Sollentuna (SE); Johan Franzén, Stockholm (SE)

(73) Assignee: St. Jude Medical, AB, Jarfalla (SE)

( * ) Notice: Subject to any disclaimer, the term of this patent is extended or adjusted under 35 U.S.C. 154(b) by 500 days.

(21) Appl. No.: 12/679,759

(22) PCT Filed: Sep. 27, 2007

(86) PCT No.: PCT/SE2007/000854
§ 371 (c)(1), (2), (4) Date: Mar. 24, 2010

(87) PCT Pub. No.: WO2009/041863
PCT Pub. Date: Apr. 2, 2009

(65) Prior Publication Data
US 2010/0204757 A1    Aug. 12, 2010

(51) Int. Cl.
*A61N 1/08* (2006.01)
(52) U.S. Cl.
USPC .................................. 607/31; 607/32; 607/60
(58) Field of Classification Search
USPC .................................. 607/31, 32, 60
See application file for complete search history.

(56) References Cited

U.S. PATENT DOCUMENTS

| | | | |
|---|---|---|---|
| 3,830,982 A | | 8/1974 | Christiansen |
| 5,350,411 A | * | 9/1994 | Ryan et al. ........................ 607/32 |
| 5,569,307 A | * | 10/1996 | Schulman et al. ............... 607/56 |
| 5,843,139 A | * | 12/1998 | Goedeke et al. ................. 607/32 |
| 6,629,776 B2 | | 10/2003 | Bell et al. |
| 7,024,245 B2 | * | 4/2006 | Lebel et al. ...................... 607/32 |
| 2003/0220673 A1 | | 11/2003 | Snell |
| 2005/0047367 A1 | * | 3/2005 | Lakkis ........................... 370/329 |
| 2006/0030902 A1 | | 2/2006 | Quiles et al. |
| 2006/0031378 A1 | | 2/2006 | Vallapureddy et al. |
| 2007/0049983 A1 | | 3/2007 | Freeberg |
| 2007/0060978 A1 | | 3/2007 | Haubrich et al. |
| 2007/0086601 A1 | | 4/2007 | Mitchler |
| 2007/0167995 A1 | * | 7/2007 | Dudding et al. ................. 607/60 |

OTHER PUBLICATIONS

"A WBAN System for Ambulatory Monitoring of Physical Activity and Health Status: Applications and Challenges," Jovanov et al., Proc. of 2005 IEEE Engineering in Medicine and Biology 27th Annual Conference, Shanghai, China (2005) pp. 3810-3813.
"Time Synchronization in Wireless Physiological Information Sensor Network," Min et al. Proc. of 2005 IEEE Engineering in Medicine and Biology 27th Annual Conference, Shanghai, China (2005) pp. 5176-5178.

* cited by examiner

*Primary Examiner* — Christopher D Koharski
*Assistant Examiner* — Natasha Patel

(57) ABSTRACT

In a medical telemetry system for synchronizing an implantable medical device to a base station of the telemetry system, a communication channel is selected for communication between the implantable medical device and the base station, and the implantable medical device is synchronized to the base station by selecting a synchronizing word associated with the selected channel, wherein at least two different communication channels within the medical telemetry system are associated with different synchronization words. By this procedure, crosstalk is eliminated.

14 Claims, 3 Drawing Sheets

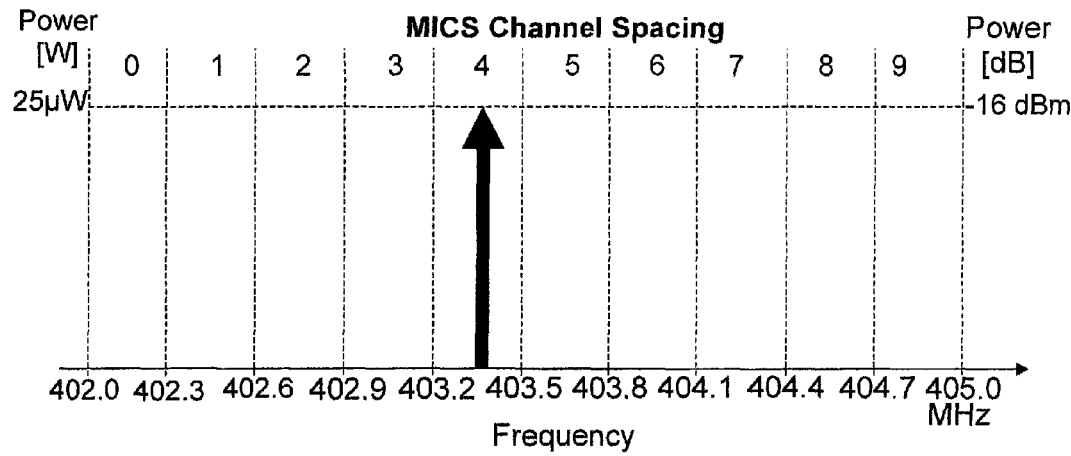
Fig. 1
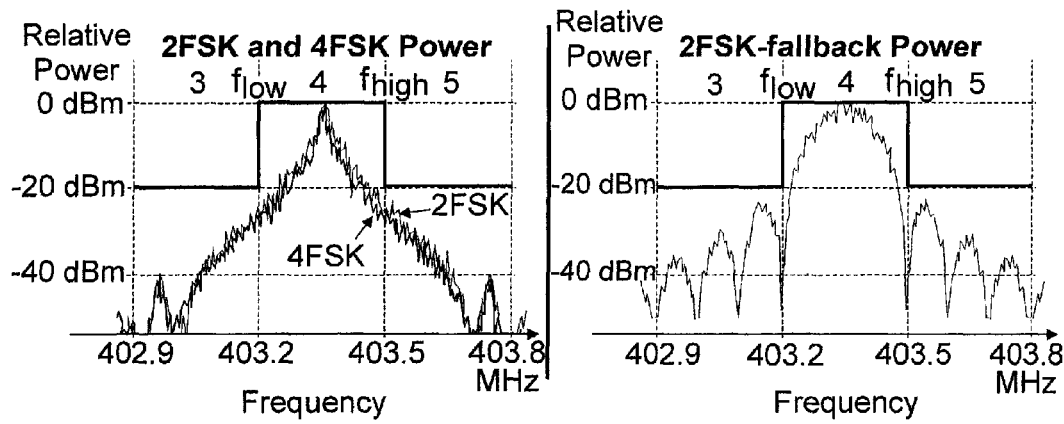
Fig. 2a                    Fig. 2b
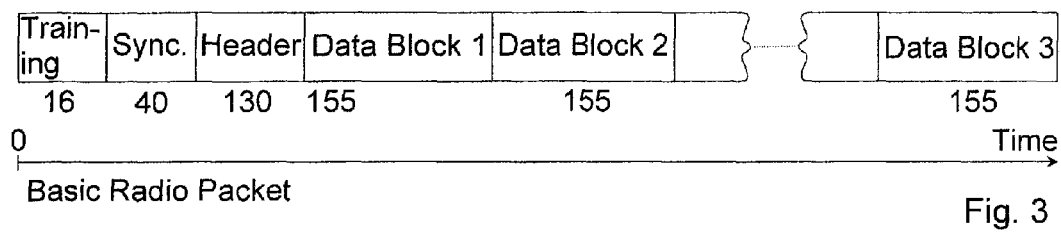
Fig. 3

SYNCHRONIZATION METHODS AND DEVICES IN TELEMETRY SYSTEM

BACKGROUND OF THE INVENTION

1. Field of the Invention

The present invention relates generally to the field of telemetry systems, and more particularly to synchronization methods within telemetry systems.

2. Description of the Prior Art

In a medical telemetry system an implantable device, such as a pacemaker, is monitored regularly by an external programming device. A physician treating the patient can thereby obtain important information, for example in order to evaluate the heart activity of the patient. The physician is also able to make changes to the settings of the implantable device if such need arises. In order to accomplish this bidirectional communication, a radio connection has to be set up between the programming device, also denoted base station (BS) or wand, of the telemetry system and the implantable device.

The communication has to fulfil different requirements, for example as stipulated by Federal Communications Commission (FCC) in the USA and by European Telecommunications Standards Institute (ETSI) in Europe. The available spectrum has to be used as efficiently as possible and the standards specify some requirements that have to be fulfilled. These requirements have to be taken into consideration when designing a MICS (Medical Implant Communication Service) system and the devices used within the system.

In particular, for medical telemetry systems, FCC MICS and ETSI ULP-AMI standards have allocated frequencies from 402 MHz to 405 MHz to be used in ten channels that are 300 kHz wide and shared among other users. Only one channel is allowed for use in a dialog from a base station to an implantable medical device (IMD), and therefore channels cannot be combined to achieve a broader channel. Further, separate channels for uplink (IMD to BS) and downlink (BS to IMD) use are not allowed. Another requirement is that the transmitter power should not exceed 25 μW (equivalent to −16 dB) in a channel. The MICS channel spacing and transmit power limit are illustrated in FIG. 1.

The standards define the radiated power as equivalent isotropic radiated power, eirp, which takes into account the properties of the radiating source. For an implanted device the radiated power of 25 μW is measured at the body surface, not at the device antenna itself. In fact, the standards postulate that the measurement is to be done with the device soaked in a specified torso phantom, filled with a fluid with electromagnetic properties that resembles the human body.

With reference to FIGS. 2a and 2b, the channel width is defined at the lower and upper frequencies, $f_{low}$ and $f_{high}$, respectively, at which the signal level is 20 dB below the maximum level of the modulated carrier. The type of modulation used in the RF telemetry transmitter benefits from this definition and uses the frequency spectrum rather extensively, but still within the limitations of the standard. The slowest communication speed uses a 2-level frequency shift keying modulation spectrum mask, even if its nearest sidelobes intrude on the adjacent channel.

A radio receiver with perfect selectivity rejects the entire signal that is not in the channel that the receiver is tuned to. However, in practice all radio receivers hear a signal from the adjacent channels. This is known as crosstalk or co-channel interference.

When a digital receiver is tuned to one channel, all data transmitted on other channels are undesired data. Unfortunately, this data can accidentally be received anyway because of the above-described crosstalk. The crosstalk behaviour may cause establishment of a communication session on different channels for two communication peers, i.e. on different channels for a BS and an IMD. This reduces the ability to read parameters and to perform fast and accurate programming. Further, having several communication sessions in an area increases the probability for crosstalk. Further yet, this is not allowed in accordance with the earlier mentioned standards.

Crosstalk may be controlled by various radio resource management schemes. Crosstalk can, for example, be combated by controlling parameters such as transmit power, channel allocation, modulation scheme, error coding scheme etc. All these methods require extensive planning resources and are performed on a system level with the objective to utilize the limited radio spectrum resources and radio network infrastructure as efficiently as possible. Although reducing crosstalk, such resource management schemes cannot entirely eliminate the crosstalk.

It would thus be desirable to provide improved means for reducing or even eliminating crosstalk between a base station and a telemetry receiver device of a telemetry system. Further, it would be desirable to provide such method, fulfilling the requirements set out by the above-mentioned standards.

SUMMARY OF THE INVENTION

It is an object of the present invention to provide methods for establishing communication between a transmitter and receiver within a medical telemetry system that fulfils regulations put on the communication.

It is another object of the invention to provide methods in a medical telemetry system in which the shortcomings of the prior art are reduced or even eliminated. In particular, it is an object of the present invention to provide methods in a medical telemetry system, whereby crosstalk between the transmitter and the receiver is eliminated or at least largely reduced.

It is still another object of the present invention to provide methods whereby undesired data from adjacent channels is not received by the receiver and wherein a synchronization between the transmitter and the receiver will fail when a packet is overheard from a different channel than the chosen communication channel.

In accordance with the invention, a method in a medical telemetry system is provided for synchronizing an implantable medical device to a base station of the telemetry system. The method includes the steps of selecting a communication channel for communication between the implantable medical device and the base station, and synchronizing the implantable medical device to the base station by selecting a synchronizing word associated with the selected channel, wherein at least two different communication channels within the medical telemetry system are associated with different synchronization words. That is, at least two of the communication channels do not use the same synchronization word. In accordance with the invention the receiver and the transmitter are reconfigured with a particular synchronization word for a particular channel. Thereby, synchronization will fail when a packet is overheard from a different channel than the wanted channel. This packet will thus not be interpreted and will not interfere with the communication. The communication methods in accordance with the invention thus provide a more reliable communication between the receiver and the transmitter of the telemetry system, and also at larger distances. Further, the use of a particular synchronization word for a specific channel increases the reliability of the communication, and thereby enables less expensive filters to be used in the receiver. Further yet, the invention may be implemented in already existing equipment, since existing hardware may be used. By using hardware already in place for synchronization, data packets that are accidentally received from adjacent channels can be successfully rejected. This is performed without compromising the quality of the synchronization and without any overhead, i.e. without using any additional bits in the data packet.

In accordance with an embodiment of the invention, the synchronization word is unique for each channel that is used within the medical telemetry system. A most reliable system is thereby provided, eliminating crosstalk on all channels.

In accordance with another embodiment of the invention, a particular synchronization word is used by two or more channels, but not by all the channels used within the system. A possibly limited availability of different synchronization words can thus be overcome. Further, the use of different synchronization words can be adapted to the particular environment of the system, and to the risks for crosstalk in that particular environment.

BRIEF DESCRIPTION OF THE DRAWINGS

FIG. 1 illustrate MICS channel spacing and transmit power limitations.

FIGS. 2a and 2b illustrate MICS spectrum mask versus FSK power spectrum.

FIG. 3 illustrates a basic radio packer for use in communication within a medical telemetry system.

DESCRIPTION OF THE PREFERRED EMBODIMENTS

Figure 4:
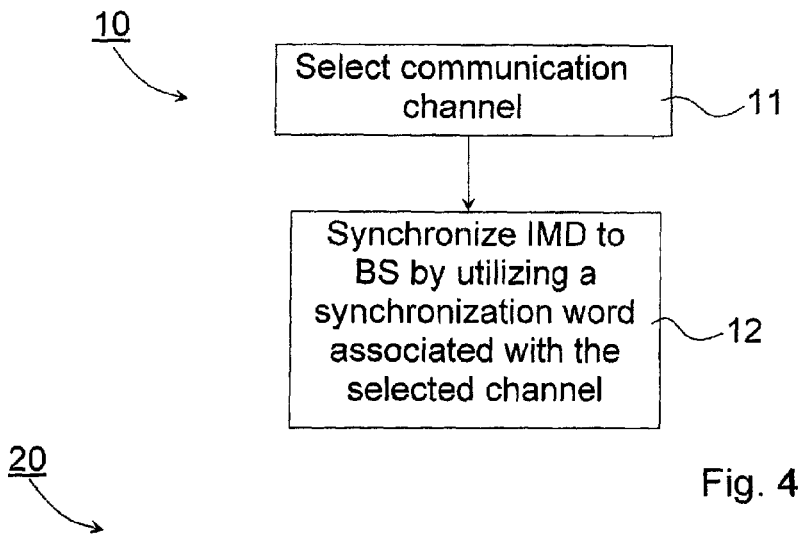
FIG. 4 illustrates steps of a first method in accordance with the invention.

The presence of sidelobes, i.e. energy transmission from the transmitter of a medical telemetry system, in the following exemplified by a base station (BS), in directions away from the main lobe of the channel can cause some interference. This is because some energy from a first channel is detected by the receiver, in the following exemplified by an implantable medical device (IMD), as well as some energy from a second channel. However, because the sidelobes have lower gain than the main beam, these transmissions can to a large extent be rejected by the IMD on the basis of their lower received signal strength. Transmissions through the sidelobe from the BS will be received at substantially lower power at the IMD and signals below a threshold value are squelched and it is possible to reject undesired transmission through or from the sidelobes.

In short, the IMD may pick up a signal on adjacent channels. In most cases, the signal on the "wrong", i.e. non-desired, channel is too weak and the filters used within the IMD are able to handle it, and the decoder of the IMD is therefore not able to decode the weaker channel. However, in dependence on, for example, type of modulation used within the system, the receiver may sometimes still decode data sent on adjacent channels. Thus, crosstalk may still occur within the telemetry system in accordance with prior art.

The present invention provides an innovative, yet easily implemented solution to this problem. In short, a number of different synchronization words used for synchronizing the IMD to the BS are utilized in accordance with the invention. For example, a particular synchronization word can be made unique for a particular channel or a particular synchronization word may be reused with suitable channel separation.

Synchronization is first described briefly in the following, in order to provide a thorough understanding of the present invention. FIG. 3 illustrates a basic radio packet for use in communication between the BS and the implantable medical device. The base station transmits control information in the transmitted data packets, including, for example, synchronization information. The IMD receives the synchronization information and synchronizes with the base station. Usually each data packet also includes a known pattern of data, a training sequence, to facilitate for the IMD to estimate the channel phase and amplitude, which is useful for decoding the symbols transmitted in the packet.

In particular, the packets of data transmitted over radio commonly contain a pre-amble consisting of the training word and the synchronization word. In FIG. 3, the first 16 bits are illustrated as being training sequence bits and the following 40 bits are illustrated as being synchronization bits, whereupon a header and a number of data blocks follow. The receiver contains hardware that can use the selected synchronization word to synchronize the receiver with the transmitter so that the first data bit is identified and decoded together with the succeeding data bits.

In accordance with the invention, each channel that is used within the medical telemetry communication system is assigned its own, preferably unique synchronization word. This is in contrast with the state of the art, in which the same synchronization word is used for all channels.

In accordance with the invention and with reference to FIG. 4, the method 10 for synchronizing the IMD to the BS includes the first step (step 11) of selecting a communication channel for communication between the IMD and the BS. The selection of a suitable channel is made in conventional manner, for example in consideration of channel signal strengths and so as to fulfil the regulations set by the earlier mentioned standards. In a second step, step 12, the IMD is synchronized to the BS. This is done by utilizing a synchronizing word associated with the selected communication channel. That is, a particular synchronization word is utilized in dependence on the selected communication channel. At least two different communication channels within the medical telemetry system are associated with different synchronization words. That is, at least two different synchronization words are used within the system.

As an example, in FIG. 1 ten channels are shown, numbered from 0 to 9. In an exemplary synchronization word reuse scheme, channel 0 may use synchronization word S0, channel 1 may use a synchronization word S1, channel 2 may use a synchronization word S2, channel 3 may use a synchronization word S3, thereafter the synchronization words may be reused: channel 4 may use the synchronization word S0, channel 5 may use the synchronization word S1 and so on. As another example, channel 0 and 9 may use the same synchronization word and the other channels may use unique synchronization words. Other reuse schemes are of course also possible.

The synchronization word is preferably unique for each communication channel that is used within the medical telemetry system. However, the availability of different synchronization words may in some cases be limited. In accordance with the invention, synchronizations words may then be reused as is described in the following.

If there are not enough different synchronization words so that each channel can obtain its own unique synchronization word, then the synchronization words may be reused in a controlled manner. For example, if it is established that there in a particular medical telemetry system is occurrences of crosstalk between every third channels, then a particular synchronization word may be reused every other channel or every fourth channel, for example. The reuse scheme of a limited set of synchronization words may thus be adapted to the particular circumstances of the telemetry system. For example, a possible reuse of synchronization words may be chosen in dependence on the occurrence of sidelobes or other signal parameters or in dependence on other conditions. Thus, a subset of the communication channels can share a synchronization word, for example two channels of a total of ten channels may use the same synchronization word.

The IMD has a receiver for reception of wireless communication from the BS. The IMD may also comprise a transmitter for transmitting information to the BS. In accordance with the invention, the IMD comprises means for selecting a particular synchronization word that is associated with a particular communication channel for use in communication between the BS and the IMD. As mentioned above, a particular synchronization word is utilized in dependence on the chosen communication channel. That is, the IMD comprises at least two different synchronization words that are associated with at least two different communication channels. Preferably, a particular synchronization word is uniquely associated with a particular communication channel.

Similarly, the BS include components for wirelessly communicating with one or more IMDs. The BS components utilize a particular synchronization word associated with a particular communication channel for use the communication between the IMD and the BS. Again, a particular synchronization word is preferably uniquely associated with a particular communication channel.

Thus, the receivers and the transmitters of the telemetry system are reconfigured with a particular synchronization word for a particular communication channel. Thereby, synchronization will fail when a packet is overheard from a different channel than the wanted channel. This packet will thus not be interpreted and will not interfere with the communication and a more reliable communication between the receiver and the transmitter of the telemetry system is provided, also at larger distances. Further, the use of a particular synchronization word for a specific channel increases the reliability of the communication, and thereby enables less expensive filters to be used in the receiver. Further yet, the invention may be implemented in already existing equipment, since existing hardware may be used. By using hardware already in place for synchronization, data packets that are accidentally received from adjacent channels can be successfully rejected. This is performed without compromising the quality of the synchronization and without any overhead, i.e. without using any additional bits in the data packet.

Figure 5:
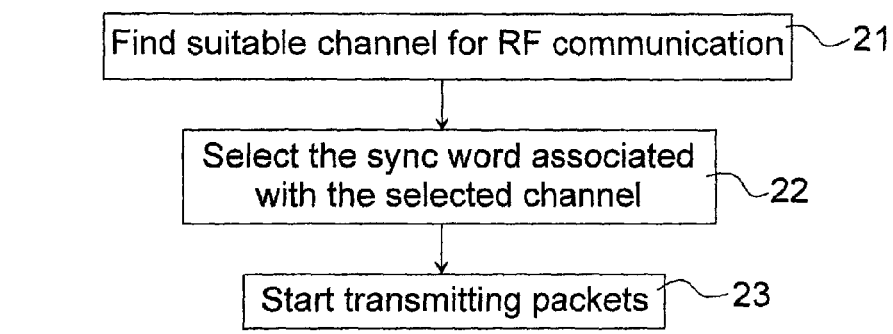
FIG. 5 illustrates steps of a second method in accordance with the invention.

The invention also encompasses a method in the BS for establishing a communication session with the IMD. FIG. 5 illustrates the steps of such method 20, wherein the BS selects a channel and sets synchronization word. The BS finds and selects, step 21, a suitable radio frequency communication channel for communication between the IMD and the BS. As mentioned earlier, such selection is made in accordance with conventional methods. In step 22, a synchronization word is utilized that is associated with the selected channel. Lastly, in step 23, the BS starts transmitting data packets to the IMD to thereby establish a communication session between the BS and the IMD.

Figure 6:
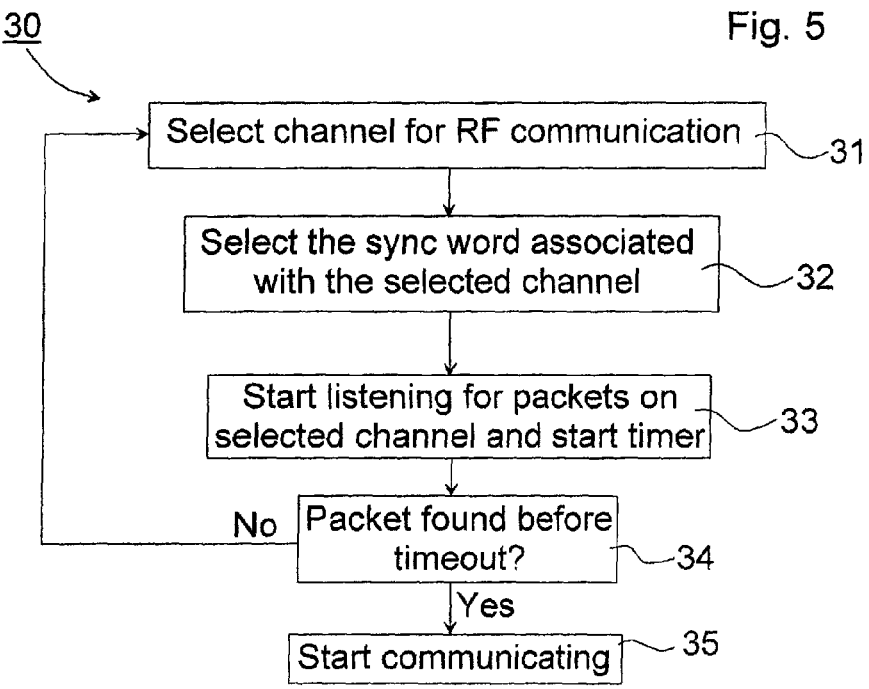
FIG. 6 illustrates steps of a third method in accordance with the invention.

The invention also encompasses a method in the IMD for establishing a communication session with the BS. FIG. 6 illustrates the steps of such method 30, wherein the IMD selects channel and selects synchronization word. The method 30 in the IMD for establishing a communication session with the BS comprises the first step, step 31, of selecting a radio frequency communication channel for communication between the IMD and the BS. As before, such selection is made in conventional manner. In step 32, a synchronization word is utilized that is associated with the selected channel. Thereafter, in step 33, the IMD starts listening for data packets from BS on the selected channel to thereby try to establish a communication session between the BS and the IMD. Further, a timer is started in this step for determining whether a set time-out period elapses in the following step. In step 34 it is determined if data packets are received on the selected channel within the time-out period. If a data packet is found on the selected channel, then a communication session is started, step 35. However, if no data packet is found on the selected channel within the time-out period, then the process returns to step 31, wherein another communication channel is selected and the steps are repeated.

Figure 7:
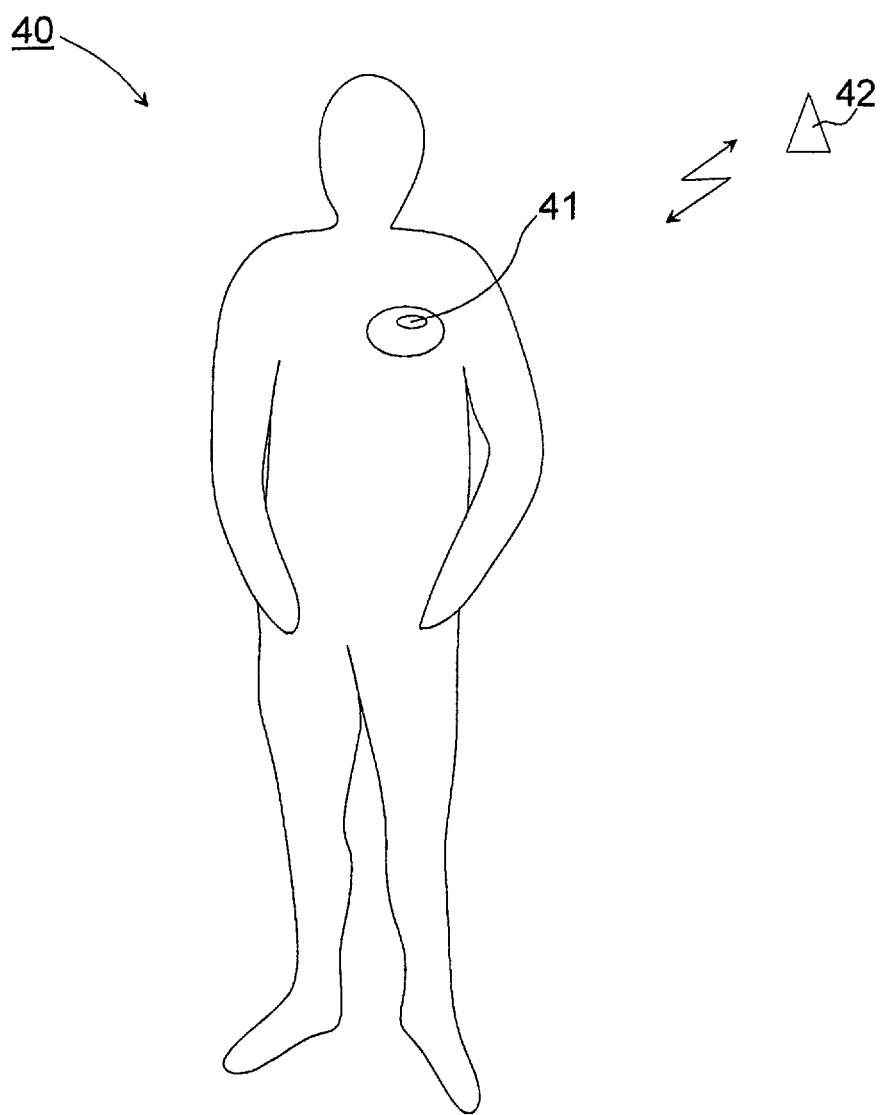
FIG. 7 illustrates a medical telemetry system in accordance with the invention.

FIG. 7 illustrates a medical telemetry system 40 in accordance with the invention. The medical telemetry system 40 comprises one or more implantable medical devices 41, for example a pacemaker, as illustrated in the figure. The implantable medical devices 41 comprise means for performing the methods as described above. The medical telemetry system 40 further comprises at least one base station 42, which comprise means for performing the methods as described above.

In summary, the invention provides an innovative way of combating co-channel interference. The transmitting and receiving ends in a medical telemetry system are reconfigured so that a unique synchronization word is used for each channel. Thereby, synchronization will be successful only for packets transmitted on the intended channel. Packets that are overheard from another channel than the one being used in a particular communication session will fail in synchronization. Thus, such packets will not be interpreted and thus will not interfere with the communication.

Although modifications and changes may be suggested by those skilled in the art, it is the intention of the inventors to embody within the patent warranted heron all changes and modifications as reasonably and properly come within the scope of their contribution to the art.

We claim as our invention:

1. A method for synchronizing an implantable medical device to a base station in a telemetry system that includes the implantable medical device and the base station, comprising the steps of:
    selecting a communication channel for communication between said implantable medical device and said base station; and
    after selecting the communication channel, synchronizing said implantable medical device to said base station by utilizing a synchronizing word associated with the selected communication channel, and by respectively associating different synchronization words with at least two different communication channels in said telemetry system.

2. A method as claimed in claim 1 comprising employing a unique synchronization word for each communication channel utilized within said medical telemetry system.

3. A method as claimed in claim 1 comprising sharing said synchronization word among a subset of all communication channels utilized within said telemetry system.

4. A method as claimed in claim 3 comprising forming said subset from at least two of said communication channels.

5. A method as claimed in claim 3 comprising reusing said synchronization word dependent on an occurrence of sidelobes.

6. An implantable medical device for use with a base station, comprising:
   a telemetry unit configured to communicate with a base station via a plurality of different communication channels;
   a selection unit configured to select a synchronization word associated with one of said communication channels for use in communication with said base station, with at least two different communication channels, among said plurality of channels, being respectively associated with different synchronization words, wherein the synchronization word is on the order of 40 bits of information; and
   a housing, containing said telemetry unit and said selection unit, configured for in vivo implantation in a subject.

7. An implantable medical device as claimed in claim 6 wherein said selection unit is configured to employ a synchronization word for each communication channel that is unique for each communication channel.

8. A base station for use in communicating with an implantable medical device, comprising:
   a telemetry unit configured to communicate with a base station via a plurality of different communication channels;
   a selection unit configured to select a synchronization word associated with one of said communication channels for use in communication with said base station, with at least two different communication channels, among said plurality of channels, being respectively associated with different synchronization words, wherein the synchronization word is on the order of 40 bits of information; and
   a housing, containing said telemetry unit and said selection unit, configured for extracorporeal placement with respect to a subject in whom said implantable medical device is implanted.

9. An implantable medical device as claimed in claim 8 wherein said selection unit is configured to employ a synchronization word for each communication channel that is unique for each communication channel.

10. A method implemented in a base station of a telemetry system for establishing a communication session between said base station and an implantable medical device within said telemetry system, comprising the steps of:
    in said base station, selecting a communication channel, from among a plurality of communication channels, for communication between said base station and said implantable medical device;
    in said base station, after selecting the communication channel, utilizing a synchronization word associated with the selected communication channel, with at least two different communication channels, among said plurality of communication channels, being associated with different synchronization words; and
    starting transmission of data packets from said base station to said implantable medical device to establish a communication session between the base station and the implantable medical device, using said synchronization word.

11. A method as claimed in claim 10 comprising employing a unique synchronization word for each communication channel utilized within said medical telemetry system.

12. A method implemented in a base station of a telemetry system for establishing a communication session between said base station and an implantable medical device within said telemetry system, comprising the steps of:
    in said implantable medical device, selecting a communication channel, from among a plurality of communication channels, for communication between said implantable medical device and said base station;
    in said implantable medical device, after selecting the communication channel, utilizing a synchronization word associated with the selected communication channel, with at least two different communication channels, among said plurality of communication channels, being associated with different synchronization words; and
    in said implantable medical device, starting to listen for data packets from said base station to establish a communication session between said base station and said implantable medical device, using said synchronization word.

13. A method as claimed in claim 12 comprising selecting a different communication channel if no data packet is received at the implantable medical device via the selected communication channel within a predetermined time period of listening for data packets.

14. A method as claimed in claim 12 comprising employing a unique synchronization word for each communication channel utilized within said medical telemetry system.

* * * * *